United States Patent [19]

Evans

[11] Patent Number: 4,940,676

[45] Date of Patent: Jul. 10, 1990

[54] CERAMIC COMPOSITIONS AND METHODS EMPLOYING SAME

[75] Inventor: James G. Evans, Boerne, Tex.

[73] Assignee: Board of Regents, The University of Texas System, Austin, Tex.

[21] Appl. No.: 207,909

[22] Filed: Jun. 16, 1988

Related U.S. Application Data

[63] Continuation of Ser. No. 51,055, May 15, 1987, abandoned.

[51] Int. Cl.$^5$ .......................... A61C 13/00; C03C 8/00
[52] U.S. Cl. ......................................... 501/16; 106/35; 264/16
[58] Field of Search ............... 501/16; 106/35; 264/16, 264/19

[56] References Cited

U.S. PATENT DOCUMENTS

| | | | |
|---|---|---|---|
| 3,880,662 | 4/1975 | Daskalon et al. | 106/35 |
| 4,024,297 | 5/1977 | Gruber | 522/37 |
| 4,046,732 | 9/1977 | Infante | 260/31.2 |
| 4,192,795 | 3/1980 | Madhavan et al. | 260/42.52 |
| 4,303,696 | 12/1981 | Brack | 522/92 |
| 4,412,015 | 10/1983 | Lustgarten | 501/69 |
| 4,414,354 | 11/1983 | Slocombe | 522/82 |
| 4,503,169 | 3/1985 | Randklev | 501/103 |
| 4,551,486 | 11/1985 | Tateosian et al. | 523/212 |
| 4,604,059 | 8/1986 | Klaus et al. | 433/2.7 |
| 4,642,126 | 2/1987 | Zador et al. | 427/54.1 |
| 4,649,062 | 3/1987 | Kosiorek et al. | 427/54.1 |
| 4,674,980 | 6/1987 | Ibsen et al. | 522/81 |

FOREIGN PATENT DOCUMENTS 81302409.8  4/1982  European Pat. Off.

OTHER PUBLICATIONS

"Direct Porcelain Repair"–Date and Author unknown.

*Primary Examiner*—Brian E. Hearn
*Assistant Examiner*—Andrew Griffis
*Attorney, Agent, or Firm*—Arnold, White & Durkee

[57] ABSTRACT

Disclosed are ceramic compositions which have been improved through the addition of a light-curing resin. Porcelain compositions are formulated to include a light-curing resin, generally of the acrylic monomer type, molded into a desired shape, and subjected to an appropriate light source to preset the molded object, for example, a porcelain inlay or margin. The present ceramic object having a thus improved integrity is transported or further manipulated, and then fired in a conventional porcelain firing oven. Ceramic compositions made in accordance with the present invention may be employed in all types of dental restoration procedures, including the fabrication of margins, inlays, crowns, laminates, as well as various non-dental applications.

13 Claims, No Drawings

CERAMIC COMPOSITIONS AND METHODS EMPLOYING SAME

This application is a continuation of application Ser. No. 051,055, filed May 15, 1987 now abandoned.

BACKGROUND

1. Field of the Invention

The present invention relates to improved ceramic compositions which include light curing resins as a binder and to methods employing such compositions, particularly in the field of restorative dentistry.

2. Description of the Related Art

In recent years, the emphasis in restorative dentistry has been toward aesthetics. Metal restorations, including fillings, inlays, onlays, crowns and bridges, are being replaced, where indicated, by more aesthetic materials. These materials are mainly resins and porcelains. Both materials may be used in restorations as a veneer or covering of metal substructures. For even more aesthetic results, restorations are being fabricated entirely of resin or porcelain. Perhaps the ultimate in cosmetic dentistry is the all resin or porcelain laminate. Discolored tooth surfaces are laminated with a thin layer of these aesthetic materials.

Both resin and porcelain are highly aesthetic materials. However, each has its own advantages and disadvantages when being considered for use in restorations. The greatest advantage that porcelain has over resins is its hardness. This property gives porcelain a greater wear resistance. Porcelain's greatest disadvantage is the difficulty encountered during the fabrication of restorations, especially those composed of all porcelain.

Dental porcelain is a fine powder of "glass-like" particles. In order to fabricate a dental restoration, water or some suitable liquid is added to the powder. A wet, sandy mix is created which can be formed into desired shapes. The porcelain particles are fused together by heat producing a solid substance similar to glass. In this manner, porcelain may be enameled to metal or simply baked into a solid mass of pure porcelain. Restorations are usually fabricated on a replica or die of the prepared tooth. Also, materials may be added to the porcelain powders which improve color and strength.

There are two properties of porcelain which complicate the fabrication of the all ceramic restoration. One is the fragile nature of the porcelain-liquid mix after shaping and prior to baking. The other complicating property is the tendency of porcelain to shrink during baking or firing. These complications can be partially overcome but require special materials and time consuming procedures.

One method of making an all ceramic restoration is known as the direct lift technique. Basically, the porcelain-liquid mix is packed and shaped on the die, replacing the missing areas. Next, the dried porcelain is lifted from the die and baked in a furnace. The particles of porcelain are thereby fused together forming the solid restoration. However, both complications mentioned previously become a factor. The dried porcelain is extremely fragile and cannot be lifted from the die without fracturing or being crushed. Secondly, the shrinkage which occurs during baking causes the restoration to distort and not properly refit on the die. These problems can be partially solved but require special materials and extra valuable time.

One such direct lift technique employs a metal foil. In such techniques, a metal foil, usually platinum or gold, is adapted to the area of the die containing the restoration. The porcelain-liquid mix is applied to the foil. After proper condensation and drying of the porcelain, the foil, supporting the porcelain, is lifted from the die and placed in the furnace for baking. After baking, the foil and porcelain restoration is returned to the die. Usually, shrinkage occurs and additional porcelain must be added and the material refired. After the proper shape and contours have been achieved, the metal foil may be removed and the all porcelain restoration is ready for placement in mouth by cementation or bonding.

Restorations using this method include inlays, onlays, crowns and laminates. This technique is also used in the fabrication of porcelain margins on crowns made by fusing porcelain to metal. This method is very difficult where very complicated tooth preparations are necessary.

Another direct lift technique is referred to as the wax additive technique. This technique is designed to make the lift off procedure possible without the use of metal foils. Powdered wax is mixed with porcelain powders instead of the water or special liquid. The die is lubricated with a separator which prevents the sticking of hot wax. The porcelain-wax mix is melted and placed on the die. After cooling, the procelain-wax is shaped by carving. It is removed and baked.

Because of extreme shrinkage and porosity caused by the eliminated wax, this method is only useful in the construction of all porcelain margins or porcelain fused to metal restorations.

A third technique, the porcelain-silica mix technique, employs the use of a liquid containing colloidal silica which is mixed with the porcelain powder. The silica causes the entire mix to harden slightly, allowing it to be lifted from a lubricated die. As with the wax additive technique, this method is generally limited to porcelain margins.

In addition to direct lift techniques, a second method used in the fabrication of all porcelain restorations is known as the refractory cast technique. This procedure involves the use of a special die material that is designed to withstand high temperatures. A die of this material is used in conjunction with the regular die. The porcelain-liquid mix is placed on the refractory die, shaped and fired without being lifted. Additional porcelain additions and refirings are usually necessary in order to compensate for shrinkage. After the desired results are achieved, the restoration is broken away from the refractory die and placed on the master die for a final check. If all is well, the restoration is ready for the mouth. If not, the whole restoration is reconstructed, starting from a new refractory die. This technique is very successful and popular but expensive. All types of restorations may be made from this technique. The construction of the refractory die is not particularly difficult but is time consuming and expensive.

The most recent method of producing all porcelain restorations is called the castable ceramics method. This technique is initiated by creating the restoration in wax. The wax pattern is lifted from the die and invested or surrounded by a mix of "plaster-like" material which is allowed to harden. A channel or opening leads from the outer surface of the investment into the wax pattern. The invested pattern is placed in an oven where the wax is eliminated through the opening. A special casting machine melts a mass of ceramic material and casts it into the opening of the investment. This glass material fills the void created by the wax pattern. After cooling, the hardened ceramic is broken out of the investment. A special oven heats the glass restoration and changes it to a more suitable ceramic form, maintaining the shape. Color is baked onto the surface of the restoration to simulate tooth color. All types of restorations are made in this manner. The fit and aesthetics are excellent. The disadvantages are the time required for fabrication and the high cost of equipment.

Thus, it is apparent that while all ceramic restorations constructed by the foregoing methods are excellent from an aesthetic standpoint, their fabrication has numerous disadvantages and limitations. Accordingly, their is a great need for improved porcelain materials and/or fabrication methods, which will allow the fabrication of ceramic objects in a manner that eliminates many of such disadvantages while allowing uses previously not possible.

SUMMARY OF THE INVENTION

Recognizing these and other disadvantages in the art, it is an object of the present invention to provide ceramic compositions having improved characteristics which render them more useful and reliable, particularly in the fabrication of dental ceramics.

It is an additional object of the invention to provide improved methods of fabricating ceramic objects, particularly porcelain ceramic objects, that require less time and have improved reliability over previously known methods.

It is a more particular object of the invention to provide ceramic compositions which exhibit less shrinkage upon baking and eliminate or reduce the need for additional add-on bakes.

The present invention involves ceramic compositions having improved properties. In particular, ceramic compositions made in accordance with the invention are readily fabricated into desired shapes, for example, porcelain inlays, in much less time and much reduced shrinkage than by previous methods with generally only a few minutes or more of hands or labor, depending on the particular object fabricated. As used herein, the term ceramic composition refers to clay or clay-like, essentially non-metallic, non-polymeric earthy compositions which may be fired at high temperatures to achieve a fusing of the material into a hardened object.

Methods and materials of the invention allow, for example, the use of the direct lift technique in the fabrication of dental porcelain ceramics without the need for metal foils or refractory die, thus resulting in further savings of time and expense. For direct fabrication, the invention presents the ability to conduct, for example, porcelain build-up directly on the tooth by a dentist. After hardening the inlay in accordance with the invention, it may then be lifted and baked, thus eliminating the need for impressions, models and dies. Inlay procedures may be completed and realized at chairside in a minimal amount of time.

These and other objects are addressed by the present invention in its most general and overall scope by means of improved ceramic compositions which include a lightcuring resin. Preferred ceramic compositions of the invention comprise as a major component a ceramic material, defined as an essentially non-metallic material capable of fusing upon firing at high temperatures, generally temperatures between about 800° and about 3500° F. Examples of such ceramic materials include, for example, porcelains, clays, white clays, kaolin compositions, phosphates, silicates, carbides, glasses, refractories, cements, aluminas, feldspar, quartz, zirconia, silicon carbide, alumina silicate, and oxides (particularly metallic oxides).

Light-curing resins are included in ceramic compositions in amounts sufficient to polymerize the resin and thus harden the ceramic material upon exposure to an appropriate light source. This allows for transportation or other further manipulations of such hardened ceramic objects with a resultant reduced risk of damage. An important distinction between light-curing resins useful in the practice of the invention, and other known polymerizing resins such as heat-curing and self-curing resins, is that light-curing resins include a polymerization activator and initiator that initiates polymerization of resin monomers in the presence of light itself, typically visible or ultraviolet light, rather than heat (e.g., heat from an infrared lamp) or a self initiating activator (e.g., dimethyl-p-toluidine and benzoyl peroxide).

Polymerization is a chemical process in which, through a series of reactions, a macromolecule, or polymer, is formed from a large number of single molecules or monomers. A compound known as an initiator is energized or activated, thus releasing free radicals. The free radicals interact with the monomer molecules causing them to chemically bond, forming the polymer. Monomers are liquid while polymers are solid. Therefore, polymerization changes the physical state from a liquid to a solid.

There are basically three ways by which the initiator may be activated to release the free radicals which cause polymerization. These activators may in the form of heat, chemicals, light or a combination of the three.

The compound benzoyl peroxide is a common initiator added to resin monomers. This compound forms free radicals when activated by temperatures above 50 degrees centigrade. Resins which are activated in this way are often referred to as "heat cured resins."

The same compound, benzoyl peroxide, may be activated chemically by the presence of an activator such as dimethyl-p-toluidine at low temperatures. Such resin combinations are termed "self cured" or "cold cured" resins.

In contrast, resins of the present invention are polymerized by their initiator being activated by light, often in combination with a chemical activator also present. Examples of suitable resins include methacrylate and dimethacrylate resins (e.g., the product of reacting bisphenol-A with glycidyl methacrylate), and other resins containing single or multiple vinyl or epoxide functionalities. These resins are made ultraviolet or visible light curing (UV cured resins have virtually disappeared from dentistry) by addition of a suitable initiator (e.g., camphoroquinone or benzil) and an activator (e.g., dimethylaminoethyl methacrylate). The formulation of such resins is well known to those skilled in the art of dental composite resin formulation. Additional light curing resins include epoxide resins with suitable initiators. Appropriate wavelengths of light generally range from about 200 to about 500 nm.

The particular light-curing resin employed is not particularly crucial and many such light-curing resins are known and readily commercially available. Most typically, light-curing resins employ resin monomers, such as acrylic (e.g., methacrylate, dimethacrylate, diacrylic and the like), vinyl or epoxide resin monomers, along with a light-activated polymerization activator and initiator such as dimethylaminoethyl methacrylate and benzil, respectively. However, it will be appreciated by those of skill in the art in light of the present disclosure that light-curing resins having other monomers and lightsensitive activators may successfully be employed in the practice of the invention.

In certain embodiments, therefore, resin monomers which include a light-reactive polymerization activator are added to ceramic compositions in amounts sufficient to polymerize when subjected to an appropriate light source. This amount will generally be determined in accordance with the particular use contemplated. Typically, ceramic powders are wetted directly with a liquid composition which includes the selected light-curing resin to achieve a workable consistency that may be further shaped or molded. When the light-curing resin is employed directly to wet the ceramic powder in this manner, the resultant mixture contains a sufficient amount of polymerizing material to harden the ceramic upon exposure to the appropriate light source.

In the fabrication of porcelain compositions suitable for use in dental restorative procedures, porcelain or, more preferably, dental porcelain powders are mixed directly with the monomer resin to achieve a desired clay consistency. Typically, a desired consistency of dental porcelain resin composition may be achieved at ratios of porcelain powder to resin of between about 8 to 1 (w/w) and about 2 to 1. More preferably, a ratio of about 6 to 1 to about 3 to 1 is employed. In the case of most bis-GMA containing resin monomers, which are generally the most readily commercially available, it has been found that a final ratio of about 6 to 1 (porcelain powder to resin) provides a very workable composition that works well in the preparation of dental restorative ceramics.

For use in dental restorative procedures it is, of course, generally preferable to use accepted dental porcelains. Most commonly, such porcelains include aluminous, feldspatic and shoulder porcelains. Generally, aluminous porcelains include varying proportions of aluminous oxides, whereas feldspatic porcelains include components of feldspar and quartz. Shoulder porcelain, as it is referred to in the art, is designed in particular for preparing all-porcelain margins. While the foregoing porcelains are preferred, particularly in the practice of dental procedures it will be apparent that other ceramic compositions may be improved in accordance with the invention so long as the qualities of the clay, such as translucence, or, alternatively, size of the object fabricated allow for sufficient light-curing of the monomer and resultant hardening of the fabricated object.

In certain further embodiments, ceramic compositions are formulated to include a desired amount of modifiers, glazes, stains and/or filler particles. As referred to herein, modifiers are porcelain powders (e.g., opaque, body or incisal) which contain a high concentration of colorants (e.g., metallic oxides) which are mixed with corresponding powders in order to modify color. Stains, usually metal oxides, are also mixed with porcelains to give desired colors. Similarly, glazes are low fusing porcelains employed to lend a glazed surface texture and color characteristics. As will be appreciated, various combinations of such additives may be employed as well.

Filler materials, as referred to herein, are glass or glass-like particles of varying sizes and shapes employed in combination with resins to improve shrinkage and integrity of fired porcelain objects. Filler particles generally include, for example, glass beads or rods, borosilicate glass powders or silica. Typically, "filled" resins are characterized in terms of microfilled and macrofilled resins. Microfilled resins include resins having generally a mean particle size of about 0.06 micrometers or less, whereas macrofilled resins include particles of between about 0.5 and about 80 micrometers in size. For most applications, filler particles are included in amounts on the order of about 20% to about 88% by weight. However, such amounts are generally a matter of choice.

Filled resins are generally thicker than unfilled resins. Thus, larger proportions of filled resins are typically added to ceramic powders than in the case of unfilled resins. For example, in preparing porcelain/filled resin compositions an initial ratio of porcelain powder to filled resin of between about 2 to 1 to about 6 to 1 is generally preferred, whereas in the case of unfilled resin porcelain compositions, a ratio of about 4 to 1 to about 8 to 1 is preferred. In both cases, however, the preferred final porcelain resin composition, after removing excess resin from the mixture, includes a ratio of between about 5 to 1 and about 7 to 1.

In general, ceramic materials are prepared in accordance with the invention by selecting a ceramic material and mixing the material with a light-curing resin to produce a ceramic resin mixture having a desired consistency and exhibiting desired light-curing properties. Ceramic compositions for use in restorative dentistry are preferably made with acceptable dental porcelains and most preferably, porcelain powders. Ceramic/resin composition may then be molded to a desired shape and subjected to appropriate light source for an appropriate length of time to cure the resin and harden the molded mixture prior to firing.

Appropriate light sources are generally determined in accordance with instructions provided by the supplier of the particular light-curing resin employed. In the case of bis-GMA type resins widely available, a visible or UV light source is generally employed for about 1 to 2 minutes for most applications. In general, light curing resins employ an activator that is activated by visible or ultraviolet light sources, for example, light sources having a wavelength of between about 360 and about 500 nm.

After light-curing the ceramic object, it may then be transported with relative ease and heated or fired sufficiently to fuse the ceramic materials. Appropriate conditions for firing of ceramic objects are well known in the art. Upon firing, the resin material is burnt out of the ceramic, thus leaving only the fused ceramic material and filler, if used, after cooling.

DETAILED DESCRIPTION OF THE PREFERRED EMBODIMENTS

The key to the present invention is the use of a special liquid binder agent in the preparation of ceramic clays and, in particular, porcelain clays. As noted previously, traditional binding agents such as water and other liquids produce fragile preset clay objects such as dental restorations. Benefits provided by the addition of wax and/or silica binders are limited. The present invention employs liquid resin monomers designed to polymerize and harden the clay when exposed to appropriate light sources. Unfilled, macrofilled or microfilled resins may be employed. However, microfilled resins tend to decrease shrinkage of the porcelain during drying and is therefore preferred for certain applications.

In the practice of an embodiment of the invention, the liquid monomer (with or without fillers) is mixed with porcelain powders. The porcelain may be of any type or brand. Preferably, a thick mix is created that can be manipulated easily, similar in some aspects to the consistency of wet clay. Compositions are prepared in this manner generally by a two step procedure wherein the ceramic material is first wetted generally with an excess of the light-curing resin, followed by condensing the mixture to remove excess moisture to obtain a workable consistency.

For die molding, an acrylic separator that sold under the trademark Rubber-Sep (George Taub) is applied to the master die. The inlay cavity of the die is filled with, for example, a porcelain-monomer mix. The mix is condensed and excess monomer is drawn out by blotting with a tissue. The semi-dried mix can then be easily carved or otherwise molded to the desired shape. Next, the mix is exposed to the appropriate light source and polymerization of the resin obtained. After the mix hardens, it is lifted from the die and, preferably, the resin burned off at about 800 to about 1000° F. prior to firing of the porcelain. This burn-off step, although not required, is typically performed in a separate burnout oven, but may also be performed by setting the object at the opening of the porcelain furnace for 20 to 30 minutes. The shaped and hardened ceramic object is then fired in a furnace according to the porcelain manufacturer's instructions.

After cooling, the restoration is tried back on the die. If slight shrinkage occurs and the restoration is not acceptable, the inlay is removed from the die. A fresh mix of a less viscous consistency is placed in the cavity prep. The inlay is forced down into the soft mix. Excess porcelain-monomer will extrude from around the solid inlay. This excess is removed and the remaining mix beneath the inlay is set using the light source. The inlay, along with the adhering unfired liner, is removed from the die and baked for a second time. Usually, a second firing is not necessary. Color may be adjusted by baking on low fusing ceramic stains or glazes.

With respect to uses relating to dental restorative ceramics, it is contemplated that porcelain-light curing resin compositions made in accordance with the present invention will be useful in virtually any situation when porcelain having improved structural and ease of presetting characteristics are desired. The invention provides particular advantages in producing intracoronal restorations, including one, two and three surface inlays. Extra coronal restorations, such as crowns, onlays and laminates, may also be made through the use of such compositions. Their use in preparing porcelain margins of ceramic-metal restorations is particularly successful.

The compositions may be supplied in forms that are particularly useful for sale, dispensing and/or storage purposes. For example, porcelain-resin mixes, even mixes of various tooth shades, can be vacuum-packed in appropriate light-opaque containers. Typically, the mixture is one having desirable workability characteristics, such as the consistency provided by a final mix (i.e., after condensation of the mix) ratio of 6 to 1 (w/w) of porcelain powder to light-curing resin. Such packages may be distributed and sold, and then easily used when needed, upon which time the appropriate shade would be selected and dispensed on the die, or directly applied to the tooth, set with light, removed and baked. No condensation of the mixture is necessary, in that the mixture is precondensed. Suitable light-opaque containers are those which do not readily pass visible or ultraviolet light and include, for example, polymers filled with carbon black.

Non-dental uses are also contemplated. For example, calcium phosphate compositions are often employed for use in filling bone. The calcium phosphate, which is a ceramic material, is usually baked into preformed shapes and sold commercially. They are cut and ground into the desired shape, sterilized and placed into position on the bone. Also, tapered cylinders are commercially made to be used to fill the sockets of extracted teeth. The present invention would allow the bone implant or socket filler to be molded directly in the area of use from a mix of calcium phosphate and resin. The molded mix is set by light, removed and baked. The method of the present invention is more accurate and saves time.

Moreover, the invention is applicable to other ceramic uses such as in the manufacture of electrical insulations, transistors and even, for example, propeller blades, where significant problems of pre-firing integrity of the shaped ceramic can exist.

The invention has application in any use where the fabrication of ceramic components having intricate shapes or critical dimensions is encountered. Among these applications are ceramic turbine blades, nozzles and bearings.

Use as ceramic repair materials is also contemplated. High temperature ceramic surfaces often crack and chip. (e.g., ceramic oven tile, muffles, etc.) A mix of ceramic refractory material and resin can be placed in the flawed area and set with light. It will remain exactly in place while the apparatus is heated.

The strength of the light cured mix allows other uses. For example, a metallic heating element of an oven can be secured in place by a light cured mix of ceramic refractory and resin. The temperature from the element will fuse the refractory material and thus securing the element in place.

The light cured mix of ceramic material and resin has the capability of being easily shaped by machinery. The machinable ceramics available today can also be shaped by machinery. However, they are extremely hard and require special hardened metal instruments and special cooling liquids. The invention would allow the shaping of the ceramic in the light cured state. After shaping, the material can be baked into its hardened state.

Ceramics are often baked in special metal molds. The invention would allow the ceramic-resin mix to be preset by light in molds made of clear plastic. The mold can be removed and the hardened mix baked in a furnace. This procedure should be more efficient, especially cost wise.

By altering the viscosity of the mix, it may be painted, sprayed, injected, cast, packed, or flowed into or onto desired area prior to baking. This would lead to many possible applications including coating surfaces, insulating, filling, etc.

A. Porcelains

There are two main types of dental porcelain. Aluminous porcelain is designed for strength. It contains a major percentage of aluminum oxide, $Al_2O_3$, a very strong material. Aluminous porcelain is typically used in the fabrication of all-porcelain restorations, for example, porcelain jacket crowns, which do not require a metal substructure. Aluminous porcelain is generally available in three different qualities. The core aluminous porcelain contains the highest percentage of aluminum oxide. It is a very strong material. Core porcelain is also opaque. This material is used to form an underlying substructure. Over the core porcelain, more translucent body and incisal porcelains are often layered. These give vitality to the restoration. The body porcelain lends the basic color to the crown. The incisal porcelain is very translucent and is designed to duplicate the thinner portions of tooth structure. Vita Dura-N, produced by Vident, is the major aluminous porcelain currently available. The invention works well with this porcelain.

Another porcelain type is feldspathic porcelain. Feldspar and quartz are the major components of this type of porcelain. This porcelain is basically designed to be baked on metal substructures. This porcelain also contains three ceramics of different qualities and uses. Opaque porcelain is designed to opaque or mask out the metal substructure. It is also chemically able to bond to certain metals. Feldspathic porcelains also typically include body and incisal porcelains. Feldspathic porcelains are used in the traditional methods of producing certain all-ceramic restorations, including inlays, onlays, and laminates. There are many brands of feldspathic porcelains available. All are compatible with the invention. Those used in the following examples include those sold under the trademarks Vita VMK-68 by Vident, Ceramco by Johnson and Johnson, Will-Ceram by Williams Gold Company, Shade Mate by Dentsply International, and Biobond by Dentsply International. Opaques, bodys, and incisals are all compatible with the invention.

Many manufacturers produce a porcelain type designed to be used in the all-porcelain margin of metal-ceramic restorations. This type of porcelain is referred to as shoulder porcelain. This porcelain is higher fusing and stronger than regular feldspathic porcelain. This porcelain is also compatible with the invention.

All commercial ceramic systems have special effects porcelains available in the form of modifiers and stains. The modifiers are mixed with opaque and body porcelains in order to change the color or shade. Stains are usually metallic oxides mixed with low fusing porcelains or glazes and are baked on the surface of porcelain to give color. Glazes are low fusing porcelains which can be baked to the surface of restorations at low temperatures to lend a glazed surface texture. All of these materials are useful with the invention.

Porcelains are commercially available with additives which give a wide range of tooth colors. The porcelains are similar. The instructions provided by the manufacturers are followed in using the various porcelains. This is in reference to firing temperatures, times, and the like.

B. Light-Curing Resins

Several types of resins are known in the art. Acrylic resin, one of thermoplastic polymers or copolymers of acrylic acid, vinyl and epoxide resins are the most common. Resin systems usually contain a powder or polymer and a liquid or monomer. The combination of these two substances, in the presence of an initiator or catalyst and activating substance, causes a chemical reaction which forms a solid substance. Prior to solidification, known as polymerization, the material is plastic and can be easily shaped. The hardened product of reaction maintains the shape. Additives give the product aesthetics desirable in dentistry.

Resin systems typically include activators or catalysts of polymerization of various types. Basically, these types include heat activated, chemically activated, and light activated resins. This invention is directed exclusively to the light activated type of catalyst. The activator is usually contained in the monomer. The monomer itself may be polymerized or hardened by the action of the activator without the presence of polymer.

Methlacrylates are the resin systems commonly used in dentistry. These can be light activated. These materials can be filled with small particles to form what are known as composite resins. These filler particles can be glass beads or rods, borosilicate glass powder or silica and include glasses containing strontium, zinc, barium, lead and other elements to make the resultant fillers radio opaque. These particles increase the viscosity of the material, making it more easily manipulated. The hardness and wearability of the product of polymerization is also increased. The resin can also be unfilled. The invention can use either filled or unfilled resins. The filled resins and, in particular, microfilled resins, decrease the shrinkage of the porcelain during baking by filling the spaces between the porcelain particles thus increasing density. The resin material, with the exception of the filler particles, completely burns out during the baking of the porcelain.

The resin used is not critical to the invention. Any resin systems utilizing light activators may be used. A resin type known as BIS-GMA was used in the experimentation of the invention. The fillers used are important. Unfilled resins produced more shrinkage than the filled resins. Filler particle size and percentage has an effect on shrinkage. The microfilled particles with a size of 0.06 microns or less cause less shrinkage than the larger macrofilled particles. One filler which may be employed is silicon dioxide. Many fillers are possible as long as they produce desirable results in shrinkage prevention and color. The unfilled and filled resins are mentioned in the examples.

C. Separators

Although not required for the practice of the present invention, separators are used when ceramic objects are fabricated on a gypsum type die and must generally be of the acrylic-gypsum type. There are several available. The tin foil substitute is one type that can be used with the invention. Al-Coat by Dentsply is one of the tin foil substitute separator which may be used with the invention. The best separator is Rubber-Sep by George Taub. This is a water soluble material which forms a thin rubber coating on the die when applied with a brush. For restorations constructed in the mouth, a separator should be used on the tooth structure which possesses desirable properties of biocompatability, lack of toxicity, absence of objectionable taste and easily manipulated (Rubber-Sep may be employed).

EXAMPLE I

Preparation of Porcelain Margins

Crowns fabricated by fusing porcelain to metal often present unaesthetic areas around their margins. This is due to two occurrences. One is the presence of a thin line of metal at the margin which generally cannot be adequately covered with porcelain. The other is the discoloration caused by the "show through" of opaque which covers the metal. The porcelain margin solves both of these problems. The metal is terminated short of the margins of the die. The porcelain fused to the metal is extended beyond the terminated metal to the margins. This porcelain edge is not supported by underlying metal.

Problems encountered when constructing porcelain margins are similar to those encountered when making all porcelain restorations. Such problems include the fragile nature of the unfired porcelain and baking shrinkage. Traditionally, porcelain margins are fabricated by the direct lift techniques using foil or silica and multiple firings.

Construction of porcelain margins is greatly simplified through the practice of the instant invention. They are made more quickly with fewer firings and fewer rejects. The description which follows discloses a particular method found by the present invention to work well, demonstrating the use of improved porcelain resin compositions in preparing such porcelain margins.

The tooth was prepared with a shoulder (or deep chamfer prep) on the facial surface extending into the proximal surfaces. Metal coping was constructed with the facial margin terminating at the junction of the shoulder and axial well. The metal was opaqued with Vita VMK-68 opaque. The opaqued coping was removed, an acrylic separator (Al-Coat by Dentsply) applied, and the coping reseated on the die.

The porcelain light curing resin mix was then prepared. Approximately 0.5 grams of Vita shoulder porcelain was mixed with about 0.2 grams of a microfilled, light curing, resin monomer (Durafill Bond by Kulzer Corp.). The mixture was blotted with a tissue to remove any excess resin and to thicken the mix to a readily-moldable, putty consistency.

A bead of the porcelain-monomer mix was placed on the exposed shoulder of the die, and extended and tapered onto the opaqued coping. The applied porcelain-monomer mix was condensed by vibrating and blotting until no more monomer could be removed. The excess flash of porcelain was then trimmed to exactly the margin of the die.

To cure the resin and thus harden the porcelain, the die and coping were placed in a Dentacolor curing unit (Kulzer Corp.) and cured for 30 seconds. The die was removed from the curing unit and the coping pulled from the due with a slight twisting motion. The resulting fit between the light-cured but unfired margin and margin of the die was then examined and found to be excellent. The coping was then fired in a furnace according to the porcelain manufacturer's instructions.

Sometimes over extensions are present and must be ground away. If any open or short extensions were observed, it was generally necessary to place fresh separator on the die, and a small amount of a more fluid porcelain-resin mixture was added where the flawed area was located. The coping was then reseated carefully, the fresh material condensed as before, excess trimmed, and allowed to light-cure for 30 seconds. The coping was then removed from the die, re-examined, and furnace fired as above.

After the coping was finished firing, it was allowed to cool and then reset on the die to check the accuracy of the fit. Typically, it has been found that one firing is sufficient, but if a flaw is discovered, the "add-on" steps discussed above may be employed. The crown was then completed using traditional porcelain techniques for porcelain fused to metal.

Porcelain margins have been successfully fabricated using Vita Shoulder Porcelain, VMK-68 body porcelain, Vita Dura N core and body porcelain, Ceramco body porcelain, Will-Ceram body porcelain, and Dentsply body porcelain. The technique is not particularly useful using opaque porcelains for the margin. The reason is that the light cannot penetrate far enough to cure thicker opaqued pieces.

EXAMPLE II

One and Two Surface Inlay: Unfilled Resin and Master Die

This experiment was conducted to produce one and two surface inlays using an unfilled resin monomer as the porcelain binder. Also, the restoration was fabricated on the master die by the direct lift technique.

The unfilled resins used were the BIS-GMA type including Dentacolor Opaque Liquid by Kulzer, Elcebond Bonding Fluid by Teledyne Hanau, Visio Bond by Espe, and Light Curing Bonding Agent by Johnson and Johnson. All materials produced the same results.

The separator (Rubbersep by George Taub) was applied to the cavity area and extended outward about 2 mm beyond the margin. A thick mixture of body porcelain-resin was prepared by mixing about 0.5 grams of body porcelain with about 0.2 grams of monomer resin. (Where maximum translucency is desired, incisal porcelain, any brand, is typically employed along with an unfilled resin liquid.)

The mix was then condensed by a tissue until a "putty-like" consistency was achieved. The porcelain-resin mix was placed in the cavity area of the die, condensed by vibrating and blotting until no more moisture was extracted, and then excess material trimmed to the margins. The anatomy of the tooth was then carved to a desired shape and placed into a Dentacolor Curing Unit (Kulzer Corp.) for 90 seconds to light-cure the resin. The inlay was removed from the die, placed in a porcelain furnace, and fired according to the porcelain manufacturer's instructions.

Through experimentation, it has been found that shrinkage may be compensated for by the following lining procedures. Reapply separator die if necessary and place a less viscous mix of porcelain-resin in the cavity area of the die. The porcelain inlay is then placed on the mix and forced into the correct position. (Vibrating aids in the seating of the inlay.) Then, condense the porcelain-resin mix and trim away excess material, cure the new liner in a light-curing unit for 90 seconds, remove inlay, and refire in furnace. Repeat steps as necessary.

The color may be adjusted using a low-fusing stain such as Vita Ceramic stain by Vident.

All porcelain inlays may be fabricated by the preceding steps. The unfilled resin bonding agents burn cleanly out of the porcelain and do not effect the color or density. Shrinkage is sometimes a problem but the relining procedure provides a practical solution.

EXAMPLE III

One and Two Surface Inlays: Microfilled Resin and Master Die

This example demonstrates the use of a microfilled light-curing resin monomer in the fabrication of porcelain inlays. The resin used was Durafill Bond (Kulzer Corp.), a bis-GMA resin, which was filled to 40% with 0.04 micron silicon dioxide particles and cured at 520 nm for 90 seconds. The inlays were fabricated as described in Example II for unfilled resins.

The microfilled Durifill Bond liquid was much more viscous than the unfilled resins employed in Example II, and produced a porcelain mix which was harder to condense to a dry state. However, the final consistency after maximum condensation was a very workable "putty" that was easily shaped or carved.

The light curing process worked similarly as when unfilled resins were employed. Although various porcelain types (i.e., body and incisal of feldspatic and aluminous porcelains) and brands were used, all porcelains produced using silicon dioxide fillers produced chalky and opaque inlays, likely due to the presence of silicon dioxide in the filler. If desired, other types of fillers such as quartz-based or even finely divided porcelain may be employed to reduce this effect. Very light shrinkage occurred during firing, with very good fits obtained after one firing.

One and two surface inlays have been typically fabricated by this technique, with very good results after only one bake. They are typically made directly from the master die by the direct lift technique. It is believed that the inclusion of filler particles is responsible for this achievement.

EXAMPLE IV

One and Two Surface Inlay: Combination Microfilled and Unfilled Resins and Master Die The purpose of this experiment was to determine if the two techniques can be used together utilizing the aesthetics of the unfilled resin procedure and the minimal shrinkage of the microfilled resin method. This was accomplished by first fabricating a base for the inlay out of the microfilled resin for accuracy of fit. The opaque base or substructure was then covered with a layer of aesthetic porcelain made from the unfilled resin.

The following steps were employed to construct the base porcelain. The die was coated with Rubbersep, and the porcelain-microfilled resin mix prepared as described in the previous examples. A layer of the mix was built up to about one-half the depth of the inlay cavity and condensed. The material was then tapered toward the margins to form a knife edge at the margins. The base was then cured for 90 seconds in the light unit, removed from the die, and fired in the porcelain furnace.

The outer layer was then fabricated as follows. The separator was checked and replaced if necessary and the base reseated on the die. A porcelain-unfilled resin mix was prepared as described in the foregoing examples, applied to the base porcelain, condensed and shaped. After curing in the light unit, the inlay was removed and fired in a porcelain furnace.

At this point, the color may be adjusted using a low fusing ceramic stain. If desirable, the surface of the base layer may be modified in color by baking on opaque modifiers or ceramic stains. This will give internal coloring.

EXAMPLE V

Three Surface Inlay: Microfilled Resin and Master Die

The use of a microfilled resin monomer has proven to greatly decrease the amount of firing shrinkage. However, the slight amount of shrinkage that does occur presents a problem in the construction of three surface inlays which enclose or surround tooth structure. Any shrinkage at all will effect the fit.

The solution of the shrinkage problem of three surface inlays has been to fabricate them in two sections and fuse them together. The procedure that can be used to accomplish this is identical to that employed in the construction of one or two surface inlays using microfilled resin with the following modifications.

After condensing the porcelain-resin mix, the inlay was cut into two sections with a fine scalpel. The two sections were then cured on the die with the light curing unit. The hardened sections were removed, baked in the furnace, and then replaced onto the die. The sections were then connected by condensing porcelain-resin mix at their junctions, cured for 90 seconds in the light curing unit, removed from the die, and baked in the porcelain furnace.

The second bake generally does not result in shrinkage. This is because shrinkage is proportional to the volume of material baked. The small amount of material used to join the two sections does not produce noticeable shrinkage.

EXAMPLE VI

Three Surface Inlay: Nonfilled Resin and Master Die

The more aesthetic porcelain inlays are constructed for three surfaces using nonfilled resin monomer. This requires the building of two sections to completion and fusing them together with the porcelain-resin mix. This procedure is similar to that described in Example V with the three surface inlays with the following modifications.

The porcelain-resin mix was condensed on the three surfaces of the die and the inlay separated into two sections with a fine scalpel. The material was then cured in the light curing unit and the two hardened sections removed from the die and fired.

To correct for shrinkage, a less viscous porcelain resin mix was placed on the die, and the two fired sections reseated and forced into proper position. The excess material which extruded from beneath the inlay sections was removed and the remaining mix was condensed. After separating into two sections with a scalpel, the sections were light-cured, removed from the die, and baked. If the fit obtained was not satisfactory, the foregoing relining steps were repeated.

When a satisfactory fit was obtained, the two sections were joined by condensing material at their junction, light-curing, removing from the die, and baking.

EXAMPLE VII

Three Surface Inlay: Combination Microfilled and Unfilled Resin and Master Die

This procedure involved the reconstruction of a porcelain-microfilled resin substructure as described earlier. The substructure was fabricated in two sections which were fused together. After the three-surface substructure was completed, a second layer, made using an unfilled resin, was fabricated. The substructure maintained the fit while the aesthetic layer was built.

EXAMPLE VIII

Inlay: Direct Technique

The preceding inlays were all fabricated using the indirect technique, with the use of a model or die representing the actual tooth. Using this invention, porcelain inlays can be constructed directly on the tooth by the dentist. One and two surface restorations would be ideal although the three surface types are possible.

The steps described in the preceding techniques are used with the following differences. The restoration is built and shaped directly in the mouth by the dentist. The separator must be of a type that can be used in the mouth and on tooth structures (e.g., Rubber-Sep). The majority of the condensation must be achieved prior to placing the porcelain-resin mix on the prepared tooth. This can be done by blotting the material on the mixing slab. Final condensation can be done on the tooth by blotting with tissue. Also, an ultrasonic scaler may be used to vibrate the material while in place on the tooth.

After shaping in the mouth, the material is set by using an intraoral light used for curing resins directly. Such lights are very common. The light-cured inlay is removed and baked as usual. Adjustment add-ons, if necessary, may be done on the tooth in a similar manner as described using the die techniques.

What is claimed is:

1. A method for preparing a ceramic composition capable of being fabricated into a ceramic object by subsequent firing, the method comprising the steps of:
   (a) selecting a ceramic material wherein the ceramic material is a porcelain;
   (b) mixing said material with a light-curing resin in proportions that will provide a ceramic resin mixture that is capable of being molded or formed into a desired shape prior to curing the resin and firing the cured ceramic resin mixture to provide the ceramic object;
   (c) molding the ceramic resin mixture to a desired shape;
   (d) light curing the resin to harden the molded mixture; and
   (e) heating the hardened ceramic mixture sufficiently to fuse the ceramic material.

2. The method of claim 1 wherein the ceramic resin mixture comprises a ratio of porcelain to resin of between about 6 to 1 (w/w) and about 3 to 1 (w/w).

3. The method of claim 1 wherein the ceramic resin mixture comprises a ratio of porcelain to resin of about 6 to 1 (w/w).

4. The method of claim 3 wherein the light-curing resin comprises a methacrylate, dimethacrylae, acrylate or diacrylic monomer.

5. The method of claim 1, wherein the hardened molded mixture is heated sufficiently to burn out the cured resin.

6. The method of claim 1 wherein the porcelain comprises a dental porcelain which includes aluminous, feldspathic or shoulder porcelain.

7. The method of claim 1 wherein the ceramic resin mixture further comprises a modifier, glaze or stain.

8. The method of claim 1 wherein the light-curing resin comprises a composite resin containing filler particles.

9. The method of claim 8 wherein the filler particles comprises microfiller particles.

10. The method of claim 8 wherein the filler particles comprise macrofiller particles.

11. The method of claim 1 wherein the light-curing resin comprises an acrylic, vinyl or epoxide monomer.

12. The method of claim 11 wherein the monomer comprises bis-GMA.

13. The method of claim 1 wherein the ceramic resin mixture comprises a ratio of porcelain to resin of between about 8 to 1 (w/w) and about 2 to 1 (w/w).

* * * * *